United States Patent
Wang et al.

(10) Patent No.: US 7,947,511 B2
(45) Date of Patent: May 24, 2011

(54) INTENSIFIED NEUTRAL LOSS TAGS AND USE THEREOF IN MASS SPECTROMETRY

(75) Inventors: Poguang Wang, Westborough, MA (US); Guodong Li, Malden, MA (US); Jianxin Gao, Dorchester, MA (US); Roger W. Giese, Quincy, MA (US); Xin Zhang, Brookline, MA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 12/479,283

(22) Filed: Jun. 5, 2009

(65) Prior Publication Data
US 2009/0242756 A1    Oct. 1, 2009

Related U.S. Application Data

(62) Division of application No. 10/741,585, filed on Dec. 19, 2003, now Pat. No. 7,556,969.

(60) Provisional application No. 60/435,179, filed on Dec. 19, 2002.

(51) Int. Cl.
C07D 207/40    (2006.01)
G01N 33/48    (2006.01)
B01D 59/44    (2006.01)

(52) U.S. Cl. ............ 436/173; 548/545; 436/86; 436/87; 436/94; 436/96

(58) Field of Classification Search ............... 436/86–95, 436/173; 548/545
See application file for complete search history.

(56) References Cited

U.S. PATENT DOCUMENTS

| 4,849,077 | A  | * | 7/1989  | Rosenthal et al. | 204/456 |
| 5,187,086 | A  | * | 2/1993  | Janda            | 435/146 |
| 7,301,018 | B2 | * | 11/2007 | Suzuki et al.    | 536/124 |
| 7,556,969 | B2 | * | 7/2009  | Wang et al.      | 436/173 |

FOREIGN PATENT DOCUMENTS
WO    WO 03/025576    3/2003

OTHER PUBLICATIONS

Kice, J. L. et al, Journal of the American Chemical Society 1966, 88, 5242-5245.*
Richter, W. J. et al, Organic Mass Spectrometry 1969, 2, 781-790.*
Benkovic, S. J. et al, Biochemistry 1970, 9, 1390-1397.*
Aimoto, S et al, Peptide Chemistry 1979, 16th, 29-34.*
Zakett, D. et al, Journal of the American Chemical Society 1979, 101, 6781-6783.*
Ikemura, H. et al, Peptide Chemistry 1980, 18th, 25-30.*
Mishima, M. et al, Memoirs of the Faculty of Science, Kyushu University, Series C: Chemistry 1986, 15, 277-286.*
Rudewicz, P. et al, Analytical Chemistry 1986, 58, 2928-2934.*
Rodriguez, M. et al, Journal of Medicinal Chemistry 1987, 30, 1366-1373.*

(Continued)

*Primary Examiner* — Arlen Soderquist
(74) *Attorney, Agent, or Firm* — Weingarten, Schurgin, Gagnebin & Lebovici LLP

(57) ABSTRACT

Ultrasensitive detection of a chemical substance (analyte) by mass spectrometry is achieved by employing a molecular tag that yields an intense parent ion and then an intense daughter ion in a multi-stage mass spectrometer.

17 Claims, 7 Drawing Sheets

OTHER PUBLICATIONS

Chowdhury, A. K. et al, Journal of the American Chemical Society 1987, 109, 5336-5343.*
Mishima, M. et al, Nippon Kagaku Kaishi 1989, 1269-1274.*
Aebersold, R. et al, Protein Science 1992, 1, 494-503.*
Mamer, O. A. et al, Journal of the American Society for Mass Spectrometry 1994, 5, 292-298.*
Wiegel, K. N. et al, International Journal of Mass Spectrometry and Ion Processes 1995, 146/147, 239-246.*
Yagami, T. et al, Rapid Communications in Mass Spectrometry 1995, 9, 1335-1341.*
Basic, C. et al, Journal of the American Society for Mass Spectrometry 1995, 6, 1211-1220.*
Zhang, G.-Q. et al, Xenobiotica 1996, 26, 541-550.*
Suzuki, S. et al, Analytical Chemistry 1996, 68, 2073-2083.*
Alexander, J. et al, Mutation Research 1997, 376, 7-12.*
Li, X. et al, Journal of the American Society for Mass Spectrometry 1997, 8, 1078-1084.*
Cheng, J.-P. et al, Journal of Organic Chemistry 1999, 64, 604-610.*
Knize, M. G. et al, Journal of Chromatography, A 2001, 914, 95-103.*
Mann, M., Journal of Mass Spectrometry, "JMS Letters", J. Mass. Spec. 2001; 36: pp. 832-833.*
Suzuki, Y. et al, Kagaku Kogyo 2003, 54, 433-438.*
Lossing, F. P. et al, Journal of Chemical Physics, 1954, 22, 1489-1492.*
Arnold, K. A. et al, Tetrahedron Letters 1988, 29, 3025-3028.*
Ouyang, X. et al, Journal of Organic Chemistry 1998, 63, 1027-1032.*
Chen, X. et al, Analytical Chemistry 1999, 71, 3118-3125.*
Sauvagnat, B. et al, Journal of Combinatorial Chemistry 2000, 2, 134-142.*
Chen, X. et al, Analytical Chemistry 2000, 72, 1134-1143.*
Munchbach, M. et al, Analytical Chemistry 2000, 72, 4047-4057.*
Wang, S. et al, Journal of Chromatography A, 2001, 924, 345-357.*
Niwayama, S. et al, Bioorganic & Medicinal Chemistry 2001, 11, 2257-2261.*
Peters, E. C. et al, Rapid Communications in Mass Spectrometry 2001, 15, 2387-2392.*
Zhao, Y.-Y. et al, Analytica Chimica Acta 2002, 468, 255-261.*
Suzuki, Y. et al, Analytical Sciences 2004, 20, 475-482.*
Ferruti, P. et al, Journal of the American Chemical Society 1970, 92, 3704-3713.*
Adackaparayil, M. et al, Journal of Organic Chemistry 1977, 42, 1655-1656.*
Keana, J. F. W., Chemical Reviews 1978, 78, 37-64.*
Jensen, N. J. et al, Desorption Mass Spectrometry, ACS Symposium Series, vol. 291, Chapter 11, 1985, 194-208.*
Keana, J. F. W. et al, Journal of Organic Chemistry 1990, 53, 3640-3647.*
Wagner, D. S. et al, Biological Mass Spectrometry 1991, 20, 419-425.*
Wang, P. et al, Analytical Chemistry 1993, 65, 3518-3520.*
Shiraishi, M. et al, Journal of Medicinal Chemistry 2000, 43, 2049-2063.*
Mann, M., Journal of Mass Spectrometry, "JMS Letters", J. Mass. Spec.. 2001; 36: pp. 832-833.
Thompson et al., "Tandem Mass Tags: A Novel Quantification Strategy for Comparative Analysis of Complex Protein Mixtures by MS/MS", Anal. Chem. 2003, 75, pp. 1895-1904.
Zhao et al., "Rapid, Sensitive Structure Analysis of Oligosaccharides", Proc. Natl. Acad. Sci. USA, vol. 94, pp. 1629-1633, Mar. 1997.
Zaja et al., "Comparison of Charged Derivatives for High Energy Collision-Induced Dissociation Tandem Mass Spectrometry", J. Am. Soc. Mass Spectrom 1995, 6, pp. 428-436.
Desai, et al., "Raney Nickel Reductions: Part V—A General Method for the Reduction of Quinones to the Corresponding Hydrocarbon Derivatives", J. Sci. Industr. Res., vol. 14B, 1955, pp. 330-334.
Johnson, David, "Alkyldimethylaminoethyl Ester Iodides for Improved Analysis of Fatty Acids by Electrospray Ionization Tandem Mass Spectrometry", Rapid Communications in Mass Spectrometry 14, pp. 2019-2024, 2000.
Zhang, et al., "Quantitative and Qualitative Determination of Estrogen Sulfates in Human Urine by Liquid Chromatography/Tandem Mass Spectrometry Using 96-Well Technology", Anal. Chem. 1999, pp. 3955-3964.
De Brabandere, et al., "Isotope Dilution-Liquid Chromatography/Electrospray Ionization-Tandem Mass Spectrometry for the Determination of Serum Thyroxine as a Potential Reference Method", Rapid Commun. Mass Spectrom 12, pp. 1099-1103, 1998.
Roth, et al., "Charge Derivatization of Peptides for Analysis by Mass Spectrometry", Mass Spectrometry Reviews, 1998, 17, pp. 255-274.
Dear, et al., "The Rapid Identification of Drug Metabolites Using Capillary Liquid Chromatography Coupled to an Ion Trap Mass Spectrometer", Rapid Commun. Mass Spectrom. 13, pp. 456-463, 1999.

* cited by examiner

INTENSIFIED NEUTRAL LOSS TAGS AND USE THEREOF IN MASS SPECTROMETRY

CROSS REFERENCE TO RELATED APPLICATIONS

This application is a divisional application of U.S. application Ser. No. 10/741,585, filed Dec. 19, 2003, now U.S. Pat. No. 7,556,969, and claims the priority of U.S. Provisional Application No. 60/435,179, filed Dec. 19, 2002, both of which are hereby incorporated by reference herein.

STATEMENT REGARDING FEDERALLY SPONSORED RESEARCH OR DEVELOPMENT

N/A

BACKGROUND OF THE INVENTION

Mass spectrometry (MS) is a powerful, widely used technique for the qualitative and quantitative analysis of chemical substances ranging from small molecules to macromolecules. In general, it is a very sensitive and specific method, and it comes in many forms, allowing gases, liquid and solid samples to be analyzed. Many of the samples are biomedical or environmental.

Among the major limitations that have held back the general usefulness of mass spectrometry, however, three are relevant here. The first limitation is that the MS signal tends to be analyte dependent, which means that some analytes are much more sensitive than others when detected by this technique. The second problem is background chemical noise, which comes primarily from the sample and often prevents high sensitivity (the ratio of signal to noise). Such noise typically is worse when the amount of analyte is lower or when the analyte is derived from a complex biological or environmental sample as opposed to having its origin as a standard. The third problem, which is related to the first, is that the optimum conditions in the mass spectrometer for high sensitivity tend to depend on the analyte.

Some analytes inherently are more sensitive than others to detection by tandem mass spectrometry because they readily form a gas phase parent ion in the mass spectrometer. For other analytes, the parent ions can undergo a favorable dissociation when activated energetically, as in a collision-induced dissociation step, to form a favorable daughter ion which may be detected relatively free of noise. A relatively intense daughter ion can arise when the compound naturally contains a bond that preferentially dissociates upon energetic activation. An example of this second property is the sensitive detection of a drug containing a labile piperidinyl-allyl bond by MS/MS (Dear et al., 1999). However, many analytes lack either of such favorable properties for sensitive detection by MS/MS.

A common strategy in mass spectrometry to increase signal strength for a poorly-responding analyte is to covalently tag the analyte with a signal-enhancing molecular group. For example, a cationic tag can be employed to enhance the signal for an analyte in an electrospray mass spectrometer or a laser desorption mass spectrometer including the technique of matrix assisted laser desorption ionization (Zhao et al., 1997). As a second example, (2-hydroxyethyl)trimethylammonium chloride (choline chloride), a saturated compound (lacking double or triple bonds), was used to derivatize fatty acids after the latter were converted to acid chlorides, and the products were detected in a tandem mass spectrometer (Johnson, 2000). Because the choline chloride tag lacked a reactivity group, it was necessary to create an acid chloride reactivity group on the analyte. A comparison of the trimethylammonium and dimethylamine derivatives showed that the former were more prone to detection by neutral loss (of trimethylamine). The application of the method to hydroxy fatty acids was especially complicated by the need to protect the hydroxy group on these acids by acetylation. Additional fragment ions also formed by neutral loss from the hydroxy fatty acids, further compromising the sensitivity. Moderate sensitivity at best was achieved.

Chemical tags have been disclosed with reactivity groups that were reacted with peptides for the purpose of enhancing the formation of sequence-specific daughter ions (Zaia et al., 1995). A complication reported by these authors was that some of the tagged peptides lost a neutral fragment from the tag. These neutral-loss cleavages were considered to be a nuisance since they competed with cleavage along the peptide chain. The latter cleavages were desired since they are the ones that provided sequence information. In most cases, the abundance of the analyte-characteristic daughter ion from neutral loss was less than 1% of the intensity of the parent ion, but in one case it was reported to be 20.9%. Since the relative abundance of the peptide ions from neutral loss was relatively low, even in the latter case, Zaia and Biemann stated, in regard to the ions from neutral loss, "These ions are not sufficiently abundant to detract from the quality of the spectrum." Of the tags studied, one that minimized neutral loss was recommended. In a review on the subject (Roth et al., 1998), it was similarly stated, "The added chemical derivative group should not fragment during analysis by tandem mass spectrometry, because that fragmentation might complicate the mass spectrum and reduce the intensity of the other fragment ion peaks." Thus, the best tags for the purpose of enhancing peptide sequencing by tandem MS have been considered to be the ones with minimal fragmentation characteristics. The general use of phosphonium tags to enhance sensitivity for mass spectrometry was also covered in this review.

Thompson et al. (2003) have introduced the concept of a molecular tag termed a "tandem mass tag" (TMT) for quantifying relative amounts of protein-derived peptides in two samples by means of tandem mass spectrometry. The relative quantitation is based on measuring the terminal charged group (sensitization group) of the tag that is released from the tagged peptide upon collision in the collision-induced-dissociation part of the mass spectrometer. It is, therefore, important for the method of Thompson et al. that the released part of the tag is lost as an ion rather than as a neutral fragment, so that it can be detected efficiently in the mass spectrometer. Pairs of tags differing in terms of isotope distribution are used, where each member of each pair of tags has the same overall content of isotopic atoms, but a different location of these atoms. One member of each pair of tags is to be used separately in a non-combined way for the tagging step for each peptide sample to be compared one against the other. After this tagging step, the two samples are combined. The detected ions for relative quantification, which are tag-derived, would be the same for every pair of peptides in the two samples being compared. Thus, these relative quantification ions provide no qualitative information about the peptides, such as their masses. There is also the option of detecting the residual peptide part based on the charge provided to it by protonation.

Finally, aryl sulfates can readily lose a $SO_3$ neutral fragment in the collision cell of a tandem mass spectrometer. For example, Zhang et al., (1999), observed that the base peak in the tandem mass spectrum of several estrogen sulfates, in which the sulfate is attached to the phenyl ring, came from loss of $SO_3$ from the parent anion. The sulfo group was similarly observed to be labile in sulfotyrosine peptides analyzed in a tandem mass spectrometer (Rappsilber et al., 2001). However, no tags were employed having an aryl sulfate moiety.

Thus, there is still need for improved analyte tags for mass spectrometry that would consistently provide increased sensitivity. In addition, a category of tags that were not dependent for their performance on characteristics of the analyte would be particularly desirable.

BRIEF SUMMARY OF THE INVENTION

The invention is directed to ultrasensitive detection of a chemical substance (analyte) by mass spectrometry by employing a molecular tag that yields an intense parent ion and then an intense daughter ion in a multi-stage mass spectrometer. Molecular tags according to the invention can be represented as XxyYZ where Z is a reactivity group, which enables XxyYZ to be attached covalently to an analyte A to form product XxyYZ-A; X is a group that bears a charge; x and y are atoms that connect X and Y by a single bond; Y includes an unsaturated group; XxyYZ-A becomes an ion that undergoes predominant cleavage in the gas phase upon energetic activation to form a neutral species Xx and an ion yYZ-A; and the charge on ion yYZ-A from this cleavage is resonance stabilized by distribution between y and the unsaturated group in Y. The structure of the molecular tag according to the invention can lead to ultrasensitive detection of the molecular tag-labeled analyte by formation of a dominating, tag-dissociated, analyte-characteristic daughter ion in high yield, both relative to other ions and on an absolute basis.

BRIEF DESCRIPTION OF THE SEVERAL VIEWS OF THE DRAWINGS

Other features and advantages of the invention will be apparent from the following description of the preferred embodiments thereof and from the claims, taken in conjunction with the accompanying drawings, in which:

DETAILED DESCRIPTION OF THE INVENTION

Figure 1:
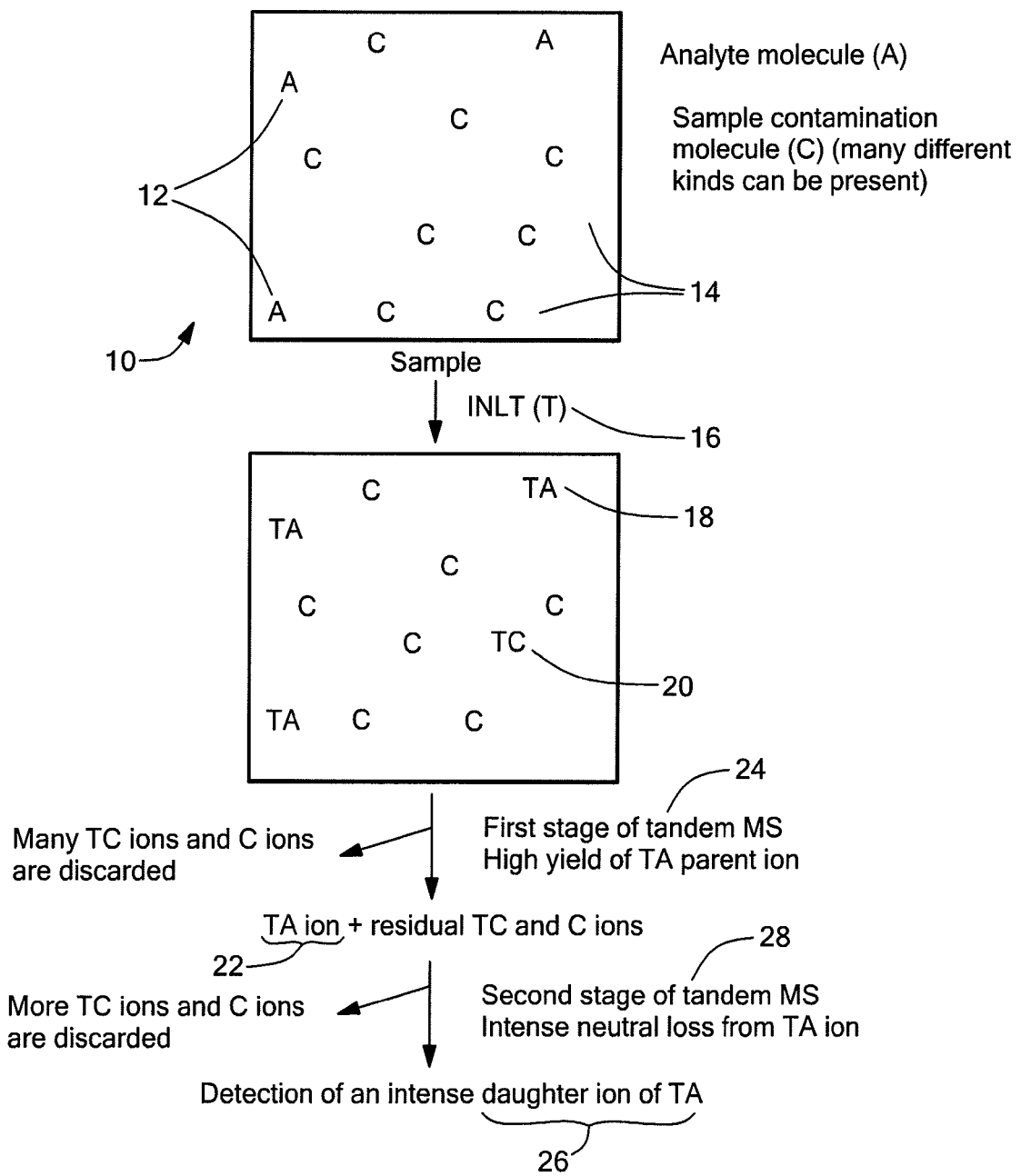
FIG. 1 shows a reaction sequence for using a molecular tag according to the invention in mass spectrometry.

This invention is directed to a technique for markedly increasing sensitivity in tandem mass spectrometry based on the use of a reagent termed "intensified neutral loss tag" (INLT or INLT tag), which is used to covalently label an analyte of interest. A method for the use of an INLT tag according to the invention is summarized in FIG. 1.

As can be seen in the reaction scheme presented, a sample (10) containing an analyte (A) (12) and (typically) Contaminants (14) is labeled with an INLT of choice (16) to form tagged analyte species TA (18) and tagged contaminant species TC (20). The tagged sample is then subjected to two (or more) stages of mass spectrometry (tandem mass spectrometry). As will be explained in more detail below, not only does the INLT tag according to the invention enhance the formation of a parent ion of the INLT-labeled analyte (TA ion) (22) in the first stage of mass spectrometry (24), but it also enhances the formation of a daughter ion (26) in the second stage (28).

INLT tags according to the invention can be represented as XxyYZ where Z is a reactivity group, which enables XxyYZ to be attached covalently to an analyte A to form product XxyYZ-A; X is a group that bears a charge; x and y are atoms (which may be substituted) that connect X and Y by a single bond; Y includes an unsaturated group; XxyYZ-A becomes an ion that undergoes predominant cleavage in the gas phase upon energetic activation to form a neutral species Xx and an ion yYZ-A; and the charge on ion yYZ-A from this cleavage is resonance stabilized by distribution between y and the unsaturated group in Y. The INLT tag provides ultrasensitivity not only because the X group enhances parent ion formation in the first stage of a two-stage mass spectrometer, but also because the xyY portion of the tag is structured to facilitate loss of the neutral compound Xx upon energetic activation of the parent ion in the second stage, producing a daughter ion bearing the same type of charge as the parent ion. The neutral loss is intensified in the INLT by means of resonance stabilization of the charge on the daughter ion. This specific enhancement of both parent and daughter ion formation can lead to ultrasensitive detection of the INLT-labeled analyte by forming a dominating, tag-dissociated, analyte-characteristic daughter ion in high yield, both relative to other ions and on an absolute basis.

Energetic activation of an XxyXZ-A ion in the mass spectrometer can be accomplished in several ways, e.g., collision with neutral gas molecules (collision-induced dissociation), collision onto a solid surface, and absorption of one or more photons. A diversity of reactivity groups can be used for the Z portion of an INLT tag. These include active esters such as N-hydroxysuccinimide (NHS) esters and carbodiimide activated carboxylic (carboxylic acid or carboxylate) groups. Other examples of reactivity groups are primary amines, hydrazides, acyl halides, alkyl halides including benzyl halides, epoxides, maleimides, imidazole, aldehydes, diazonium, isothiocyanate, sulfhydryl, carbene and nitrene.

In more detail, use of the INLT tag according to the invention increases sensitivity by mass spectrometry in seven complementary and overlapping ways, keeping in mind that sensitivity is the ratio of signal to noise. First, noise is reduced by use of the INLT because many contaminants will be discarded in the first stage of the mass spectrometer where selection of a parent ion takes place. Second, of those contaminants that remain after the first stage, many will be discarded in the second stage of the mass spectrometer since they do not give a fragment ion equivalent in mass to that of the daughter ion created by the selected neutral loss. Third, the ease of selected neutral loss of the Xx fragment using this method means that fragmentation in the analyte portion of the INLT-labeled analyte molecule is reduced. Selected neutral loss incorporates the energy available from energetic activation in the second stage for preferential cleavage of the x-y bond of the tag portion before this energy can break other bonds in the INLT-labeled analyte parent ion. The yield of the selected daughter ion, therefore, is high relative to other ions, giving a mass spectrum dominated by the selected daughter ion. In turn, this means that a low activation energy can be used, which minimizes fragmentation and, therefore, noise from contaminating compounds. Fourth, the high yield of the selected daughter ion from the selected parent ion thereby produces an intense mass spectrum signal in absolute terms for the selected daughter ion. Fifth, both the parent ion and the selected daughter ion are characteristic of the analyte. This means that their masses are dependent on the analyte, which not only is important for identifying analytes, but also for distinguishing the INLT-labeled analyte from other compounds (chemical noise) in the mass spectrometer. Sixth, the method of the invention allows one to control the mass of the parent and daughter ion to increase sensitivity. For example, this can be accomplished by varying the substituents on the ammonium or phosphonium group of an INLT tag carrying those groups. This can also be done, e.g., for carboxylic and sulphate INLT tags, by relying on stable isotopes such as $^2$H, $^{13}$C or $^{18}$O. Thus, the method enables the daughter ions to be placed at noise-free masses in the mass spectrum in order to overcome known interferences. Seventh, use of an INLT allows the parent and daughter ions for a small sized analyte to be raised to a higher mass that is more free of background noise in the mass spectrometer.

Intensifying a selected neutral loss in formation of the daughter ion is a key feature of the method of the invention, which, in combination with enhancement of parent ion yield, can lead to ultrasensitivity not just for standard trace analytes, but for trace analytes in real samples. Intensification of a selected neutral loss from an INLT tagged analyte parent ion, in combination with favorable formation of the parent ion, is achieved by setting up resonance stabilization of the charge that arises in the remaining portion of the INLT from the selected neutral loss. This resonance stabilization is based on including an unsaturated moiety in the Y portion of tag XxyYZ in close proximity to the y atom so that the charge that develops on y during the selected breakage of the xy bond during daughter ion formation will be stabilized via conjugated sharing with the unsaturated moiety. For example, choosing a nitrogen atom for x that is made cationic by alkyl, aryl or proton substitution, an alkyl- or hydrogen-substituted carbon for y, and phenyl for Y leads to a benzyl cation as the yYZ-A ion when the xy bond breaks from neutral loss of the Xx group. Other options for Y in this case are ethenyl (forming an allylic cation) and ethynyl (forming a propargyl cation). Choosing an oxygen atom for x, a sulphonyloxy (sulphonate group) ($SO_3^-$) for X (giving a sulfate), and a phenyl group for Y leads to a phenolate anion as the yYZ-A ion when the xy bond breaks with neutral loss of sulfur trioxide. A carboxylate group ($CO_2^-$) can also be used instead of a sulphate.

Examples of instruments that can be used to provide tandem MS in the method of this invention include triple quadrupole, ion trap (e.g., quadrupole or ion cyclotron) and time-of-flight/time-of-flight mass spectrometers. An ion trap mass spectrometer is preferred, especially a conventional (Paul) ion trap or a linear ion trap, including ion trap/time-of-flight mass spectrometer or an ion trap/ion trap mass spectrometer. Multiple analytes can be detected together by INLT labeling followed by tandem mass spectrometry, where multiple daughter ions then are detected together.

It is generally preferred to employ an INLT that forms one or more relatively unique neutral products in the dissociation step of the INLT technique, so that the loss of more common neutral products such as $H_2O$ from background parent ions isobaric with the targeted parent ion do not interfere. For example, an unusual neutral product such as triethylamine can be formed from an INLT that contains a $(Et)_3N^+CH_2$-phenyl moiety. It is generally preferred to employ an INLT where the ionization and dissociation of the INLT-labeled substance of interest is independent of proton loss or adduction.

Nonisotopic and isotopic forms of an INLT can be used in combination to add further specificity to the measurement. First the analyte of interest is reacted with a mixture of the two tags. Then, after introduction of the reacted sample into the mass spectrometer, the two parent ions, isotopic and nonisotopic, are both selected for energetic activation. If the expected ratio of exclusive daughter ions is not observed for a given analyte, then the presence of an interference or abnormal condition in the mass spectrometer is revealed. Along these same lines, the opportunity to substitute one daughter tag for another to measure an analyte creates an opportunity to vary the mass of the final daughter ion(s) that is observed, until a mass is found where no background interfering ions are present.

One can also use a pair of INLTs that give the same mass for a given parent ion but different masses for the daughter ions to enhance sensitivity or specificity. This can be accomplished by preparing pairs of INLT that both contain the same number of isotopic atoms, yet differ in the substitution sites such that only one member of each pair forms an isotopically-labeled daughter ion. For example, $(^{13}C^2H_3)(CH_3)_2N^+CH_2C_6H_4R$ and $(CH_3)_3N^+CH_2C_6D_4R$ can be used in this way, where R comprises a reactivity group such as an N-hydroxysuccinmide ester. While these two INLTs have the same mass, they would give daughter ions of different masses.

It is attractive to use INLT tags as labels because of their ultrasensitivity to multiplexing in ligand assays, such as immunoassays and hybridization assays. A cocktail of INLT-labeled reagents could be used where each reagent gives one or more parent or daughter ions having a unique mass. To detect these INLT-labeled reagents simultaneously in the case where the parent ions in the detection process differ in their masses, multiple parent ions would be selected in the first stage of the tandem mass spectrometer for dissociation and detection in the second stage.

A major advantage of the INLT technique is that it removes or mitigates the need to tune the ion source and collision conditions to optimize the sensitivity of the method for each analyte. This is especially important in the detection of unknown analytes at trace levels, where the opportunity to tune these conditions may not exist, or be very limited. It is also very important in multi-analyte detection.

The INLT technique can be advantageous for structural characterization, e.g., of nucleotides or peptides, since it can give rise to unique daughter ions in the second stage of a tandem mass spectrometer that, in turn, can be fragmented into structurally informative and unique granddaughter ions in the third or higher stages of tandem MS. Further, since the INLT technique provides daughter ions of high intensity, it can help to minimize the inherent problem of progressively weak signals with each stage of tandem MS.

The method of the invention also can be practiced by taking advantage of the technique of employing a $R_3QCX_2$-aryl, $R_3QCX_2$-alkenyl or $R_3QCX_2$-alkynyl moiety as part of the INLT, where X is selected from H, D, alkyl, alkenyl, alkynyl or aryl. Q is N or P, and at least one R is alkyl, alkenyl, alkynyl or aryl. The alkenyl, alkynyl, or aryl group can be substituted with other groups. The invention further can be practiced with carboxylic (carboxylic acid or carboxylate) versions of INLT tags in which a keto group is located β to the carboxylic group, e.g., where the XxyY part of the tag is $HO_2CCH_2CO$, $HO_2CNHCO$ or $HO_2COCO$, and the carboxylic group is in a carboxylate form.

In one form of this invention, moieties such as allyl, benzyl and propargyl are used as part of a molecular group that contains a dissociative-prone bond leading to a carbocation in the second stage of the tandem MS measurement. In each case, the carbocation arises at a carbon which, in turn, is connected to an activating group (namely alkenyl for allyl, phenyl for benzyl, and alkynyl for propargyl). Examples of other activating groups or cores of groups that can be used in the same or similar way are naphthyl and other aryls, indole or imidazole and other heteroaryls, ferrocene or other organometallics, cyclopropyl, ethereal oxygen, conjugated polyalkenyl, allenyl, norbornenyl, norbornadienyl, N=C, N=N, NH—N=C, and related species including combinations of these and the alkenyl, phenyl and alkynyl groups such as styryl. The tendency of these groups to enhance the formation of carbocations can also be increased by adding substituents such as alkoxy or dialkylamino. For example, electron-donating groups (incorporated herein by reference) in ortho or para positions stabilize arylmethyl cations (Goldacre et al., 1949).

It is an option to utilize a high spray voltage when the invention is practiced with electrospray mass spectrometry in order to enhance the formation of an intense parent ion in the first stage of a tandem MS instrument. While the high spray voltage tends to increase the formation of background ions, the net result can be enhanced sensitivity because of the ease of forming a daughter ion in the INLT technique, especially when it entails the co-formation of an unusual neutral product, and especially when a daughter ion is formed at a relatively high mass.

Correspondingly, when the INLT technique is practiced in a laser desorption mass spectrometer including use of matrix-assisted techniques, it is an option to employ a high fluence laser desorption pulse. While a high spray voltage in electrospray or a high laser fluence in laser desorption can decrease sensitivity in ordinary forms of these techniques (because of increased noise), it can increase sensitivity in the INLT technique according to the invention.

The following examples are presented to illustrate the advantages of the present invention and to assist one of ordinary skill in making and using the same. These examples are not intended in any way otherwise to limit the scope of the disclosure.

All chemicals were used as received unless otherwise stated. $^1$H NMR was recorded on a Varian 300 MHz Mercury-300 spectrometer.

Figure 2:
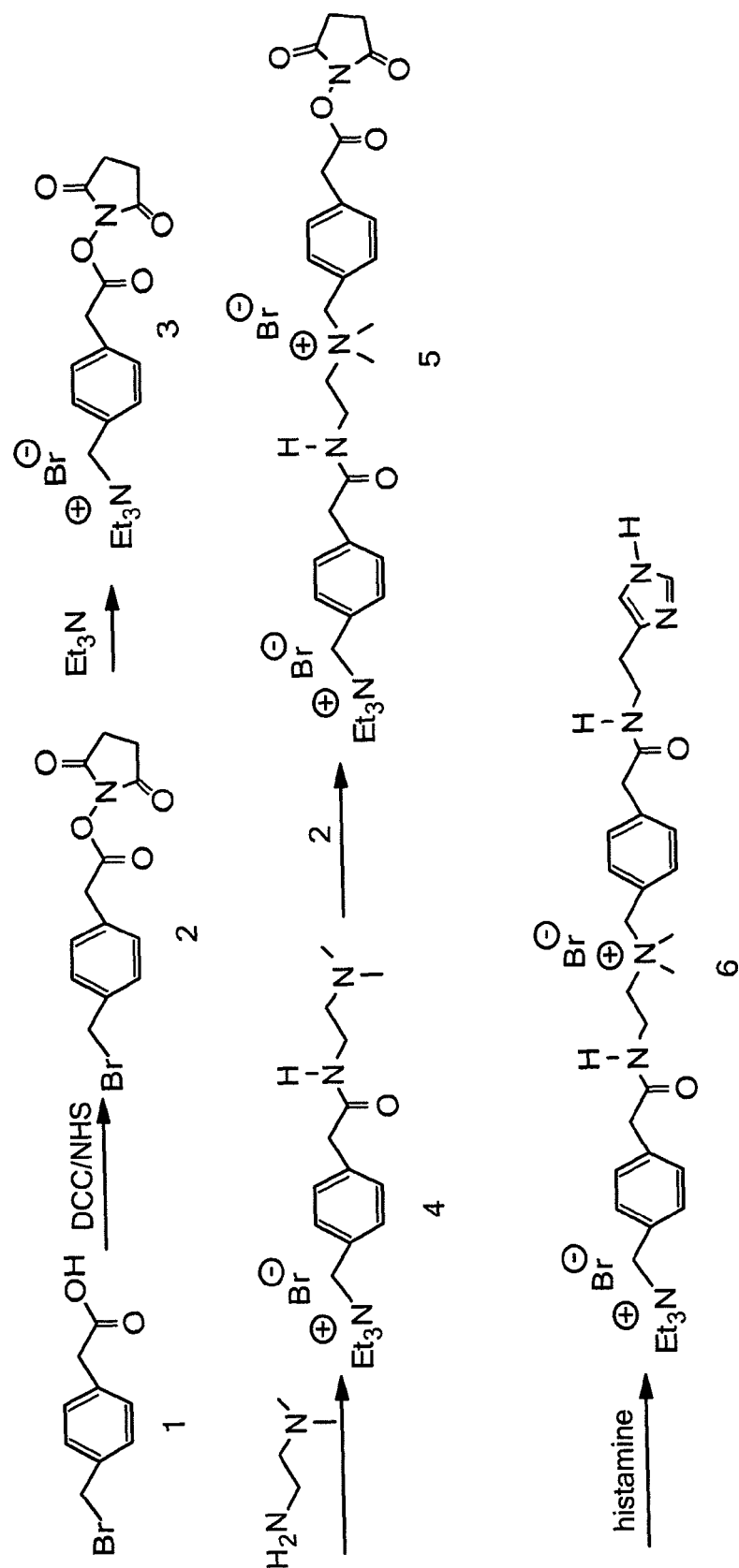
FIG. 2 shows a reaction sequence for the synthesis of certain molecular tags (3, 5 and 6) according to the invention.
Figure 3:
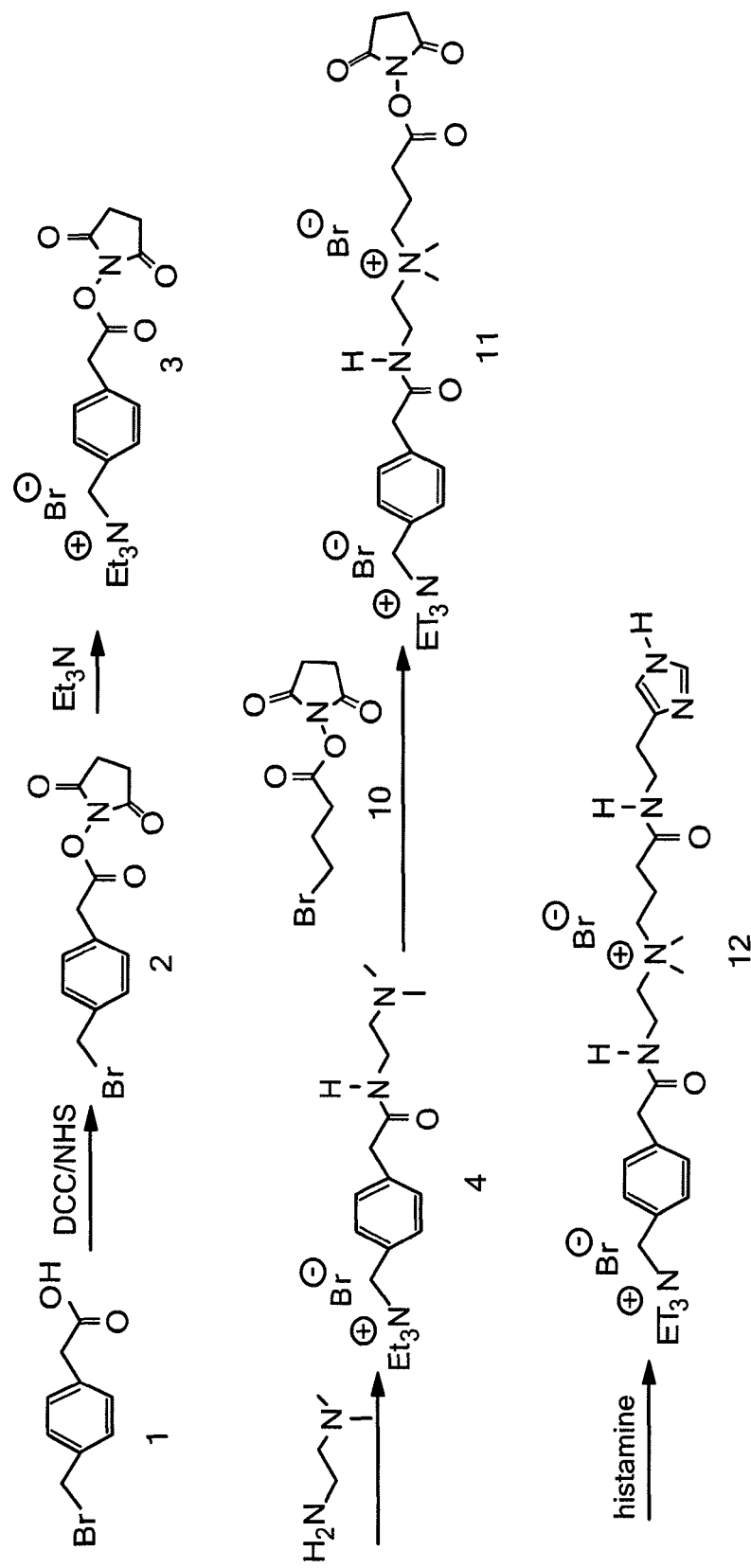
FIG. 3 shows a reaction sequence for the synthesis of additional molecular tags (11 and 12) according to the invention.
Figure 4:
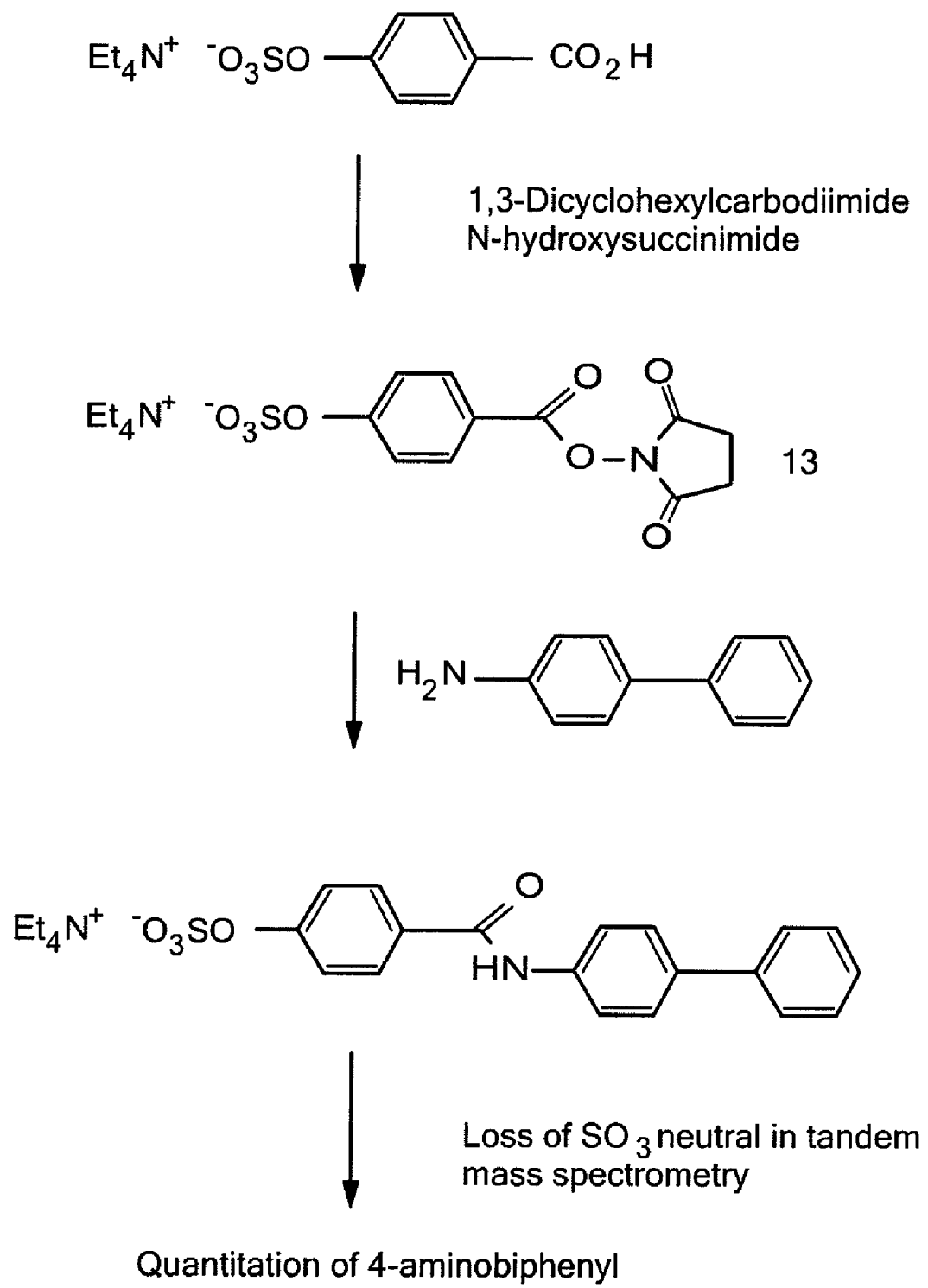
FIG. 4 shows the detection of 4-aminobiphenyl using molecular tag 13 according to the invention.
Figure 5:
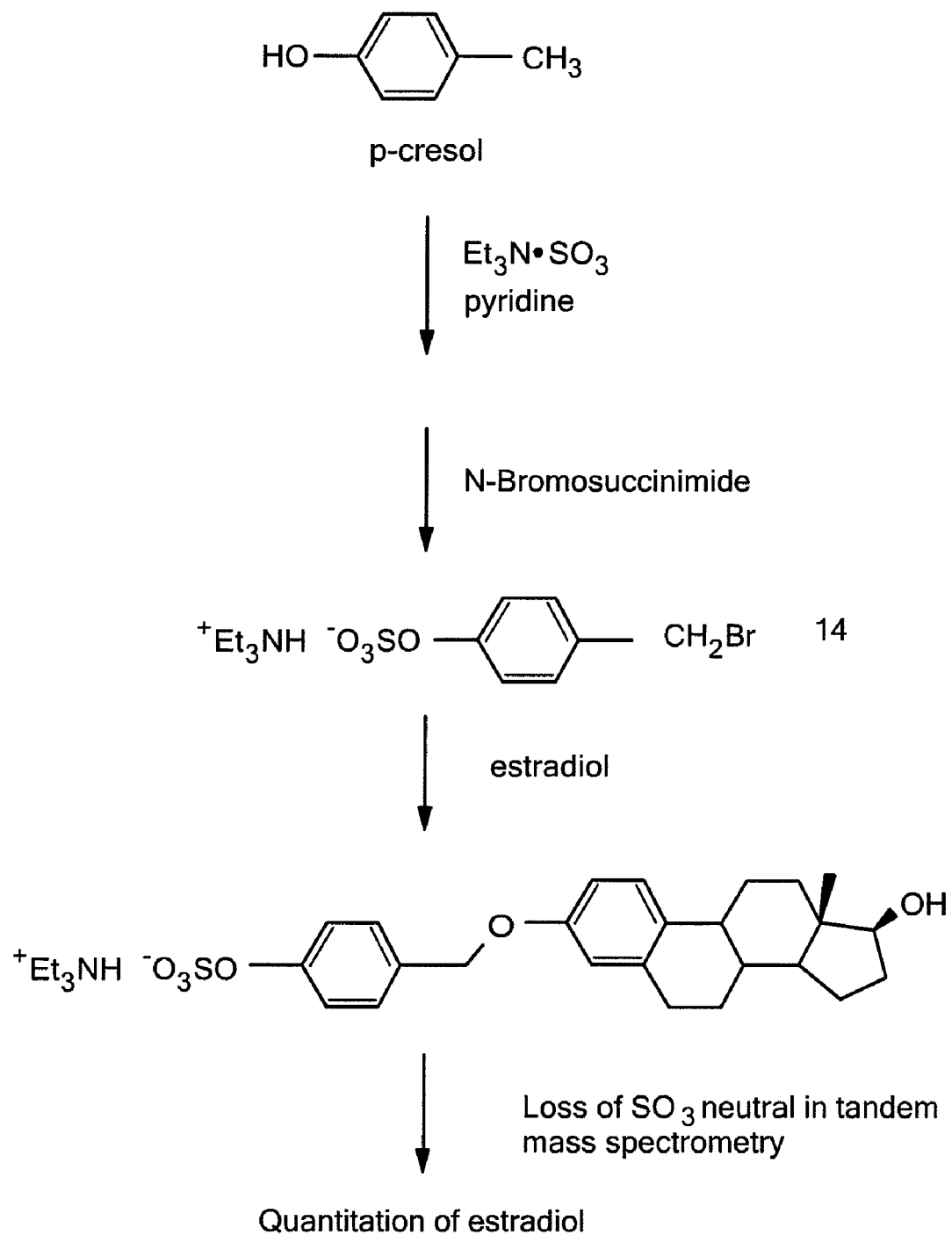
FIG. 5 shows the detection of estradiol using molecular tag 14 according to the invention.

Referring to FIG. 2, a summary of the reaction sequence used to synthesize specific INLT tags according to the invention 3, 5 and 6 is shown. Commercially available (Aldrich) (4-bromomethyl) phenyl acetic acid was converted to a corresponding NHS active ester and then the bromo atom was replaced with triethylamine, yielding INLT tag 3. Reaction of 3 with N,N-dimethylethylenediamine gave intermediate 4, which in turn was coupled with 2 to give INLT tag 5. Also, INLT tag 6, having an imidazole reactivity group, was then prepared by reacting 5 with histamine. The similar conversion of compound 4 into INLT tags 11 and 12 was accomplished as shown in FIG. 3. As seen, in this case, compound 4 was reacted with the NHS ester of 4-bromobutyric acid to give 11, and the latter compound was then coupled to histamine to give 12. Synthesis of INLT tags 13 and 14 is shown in FIGS. 4 and 5, respectively. On INLT tags 3, 5, 6, 11 and 12 any of the ethyl residues on the terminal triethylammonium group can be replaced by an alkyl (e.g., methyl, propyl or butyl), aryl, alkenyl or alkynyl group.

The specific reaction conditions to produce the indicated INLT tags according to the invention are given below:

4-Bromomethylphenyl acetic acid NHS ester (2)

4-Bromomethyl phenylacetic acid (472 mg, 2 mmol) was dissolved in 3 ml acetonitrile (MeCN) and 2 ml tetrahydrofuran (THF). N-hydroxysuccinimide (NHS) (253 mg, 2.2 mmol) and dicyclohexylcarbodiimide (416 mg, 2 mmol) were added. The mixture was stirred overnight at room temperature. Dicyclohexylurea (DCU) was filtered off, solvents were evaporated. Yield of 2 was 632 mg, which contained a little DCU. The pure 2 can be obtained using the following method: 2 is dissolved in acetonitrile and methanol, then the solution is sucked by vacuum through a fritted funnel, and 2 crystallized out. $^1$H NMR ($CD_2OCD_3$, ppm): 2.87 (s, 4H), 4.06 (s, 2H), 4.66 (s, 2H), 7.39-7.49 (m, 4H).

4-(Triethylamino)methyl phenylacetic acid NHS ester (3)

Compound 2 (850 mg, 2.6 mmol) was dissolved in 20 ml dry THF. Triethylamine (210 µl) was added. A white solid precipitated instantly. After 15 minutes, the solid was filtered off, and dried under vacuum. Yield of 3 was 1.09 g $^1$H NMR ($CD_3OD$, ppm): 1.42 (t, 9H, J=7.2 Hz), 2.83 (s, 4H), 3.26 (q, 6H, J=7.2 Hz), 4.09 (s, 2H), 4.48 (s, 2H), 7.54 (s, 4H).

2'-[4-(Triethylamino)methyl phenyl acetamido]-ethyl-N,N-dimethyl amine (4)

Compound 3 (854 mg, 2 mmol) was dissolved in 10 ml MeCN. N,N-dimethylethylenediamine (234 µl) and triethylamine (836 µl) were added respectively. The solution was stirred for one hour at room temperature, and then evaporated. Ethyl ether was added, the mixture was shaken, and the ether was decanted. The oily residue was vacuum dried. A mixture of compound 4 and NHS (1:1 mole ratio) was obtained, and was used for further reaction without separation. $^1$H NMR ($CD_3OD$, ppm): 1.42 (t, 9H, J=7.2 Hz), 2.35 (s, 6H), 2.56 (t, 2H, J=6.6 Hz), 2.63 (s, 4H, from N-hydroxysuccinimide), 3.25 (q, 6H, J=7.2 Hz), 3.35 (t, 2H, J=6.6 Hz), 3.59 (s, 2H), 4.46 (s, 2H), 7.41-7.52 (m, 4H).

4"-{2'-[4-(Triethylamino)methyl phenyl acetamido]-ethyl-N,N-dimethylamino methyl}phenyl acetic acid NHS ester (5)

The mixture of compound 4 and NHS from the previous step was dissolved in 10 ml dry MeCN. compound 2 (590 mg, 1.9 mmol) was added. A sticky gel was separated from the solvent. After overnight stirring at room temperature, MeCN was decanted. The residue was dried under vacuum and was identified as 5 by proton NMR.

Amine Conjugate of 5 with the Primary Amino Group of Histamine (6).

Compound 5 was dissolved in 5 ml dry dimethylformamide (DMF). Histamine (200 mg, 1.8 mmol) and triethylamine (753 µl) in ml MeCN/water (50/50, v/v) were added to DMF solution. The mixture was stirred for one hour at room temperature, and diluted with acetone. Solvents were decanted. The residue was dissolved again in a minimum amount of methanol and diluted with acetone. Solvents were decanted again. Finally, the residue was purified by reverse phase C2-Si (EM sciences) flash chromatography. After sample was loaded onto the column, the columns was washed by MeCN, then eluted with MeCN/methanol (80/20, v/v).

Yield of 6 is 260 mg. $^1$H NMR of 6 (D$_2$O, ppm): 1.20 (t, 9H, J=7.2 Hz), 2.72 (t, 2H, J=6.3 Hz) 2.86 (s, 6H), 2.99 (q, 6H, J=7.2 Hz), 3.24-3.39 9 (m, 4H), 3.43 (s, 2H), 3.53 (s, 2H), 3.63 (t, 2H, J=6.3 Hz), 4.16 (s, 2H), 4.24 (s, 2H), 6.88 (s, 1H), 7.12-7.40 (m, 8H), 8.08 (s, 1H).

4-Bromobutyric acid NHS ester (10)

4-Bromobutyric acid (3.34 g, 20 mmol) was dissolved in 25 ml methylene chloride and 20 ml acetonitrile. N-hydroxysuccinimide (2.37 g 20 mmol) and dicyclohexylcarbodiimide (4.16 g, 20 mmol) were added respectively. The mixture was stirred for two hours at room temperature. Dicyclohexylurea was filtered off. Solvents were evaporated. The resulting dark yellow oil was subjected to flash chromatography purification using ethyl acetate/hexane/acetic acid (40/60/1, v/v). After evaporation of solvents, a white solid was obtained. The yield of 10 was 4.04 g.

4''-{2'-[4-(Triethylamino)methyl phenylacetamido] ethyl-N,N-dimethylamino}butyric acid NHS ester (11)

Compound 10 (149 mg, 0.56 mmol) and a mixture of 4 and N-hydroxysuccinimide (1:1 mole ratio) (240 mg, 0.47 mmol) in 4 ml dry acetonitrile (distilled over phosphrous pentoxide) were placed in a pressure tube. The tube was heated to 80-90 degree (C) overnight, then cooled to room temperature, and diluted with THF. Solvents were decanted. The residue was dried under vacuum. Yield of 11 was 240 mg.

Amide Conjugate of (11) with the Primary Amino Group of Histamine (12).

Compound 11 (225 mg) was dissolved in 2 ml dry DMF. Histamine (38 mg) and triethylamine (140 microliters) were dissolved in 1 ml acetonitrile/water (50/50, v/v). These two solutions were combined and stirred for one hour at room temperature. After concentration by evaporation, the residue was diluted with acetone and a sticky gel precipitated. The mixture was filtered through a fritted funnel packed with white quartz sand. The sand was eluted with methanol. After evaporation of methanol, the residue was dried under vacuum. The yield of 12 was 47 mg.

4-(Sulfonyloxy)benzoic acid NHS ester (13)

p-Hydroxybenzoic acid was converted to 4-(sulfonyloxy) benzoic acid with pyridine sulfur trioxide in pyridine as described (N. B. Desai, V. Rananathan & K. Venktaraman, *Raney Nickel Reductions: Part V-A General Method for the Reduction of Quinones to the Corresponding Hydrocarbon Derivatives*, J. Sci. Industr. Res., 14B, 1955, 330-334). In turn, this intermediate can be converted into product 13 by reaction with 1,3-dicyclohexylcarbodiimide and N-hydroxysuccinimide, or with 1-[(3-dimethylamino)propyl]-3-ethylcarbodiimide hydrochloride and N-hydroxysuccinimide.

4-(Sulfonyloxy)benzyl bromide (14)

p-Cresol can be reacted with pyridine sulfur trioxide in pyridine to form 4-(sulfonyloxy)toluene, which in turn can be converted into product 14 by reaction with N-bromosuccinimide.

EXAMPLE 1

Detection of Amino-Biphenyl Using the Method of the Invention

Compound 13 was coupled to 4-aminobiphenyl analyte in the presence of a water soluble carbodiimide, such as 1-ethyl-3-(3-dimethylaminopropyl) carbodiimide. The resulting conjugate can be detected by electrospray tandem mass spectrometry by detecting the phenolate-containing daughter ion produced by collision-induced dissociation of the parent ion with loss of SO$_3$ neutral. This assay is illustrated in FIG. 4.

EXAMPLE 2

Detection of Estradiol Analyte Using the Method of the Invention

Estradiol analyte is detected by derivatization with compound 14 followed by electrospray tandem mass spectrometry, relying on the measurement of the daughter anion formed by loss of SO$_3$ as the neutral fragment. This example is illustrated in FIG. 5.

EXAMPLE 3

Figure 6:
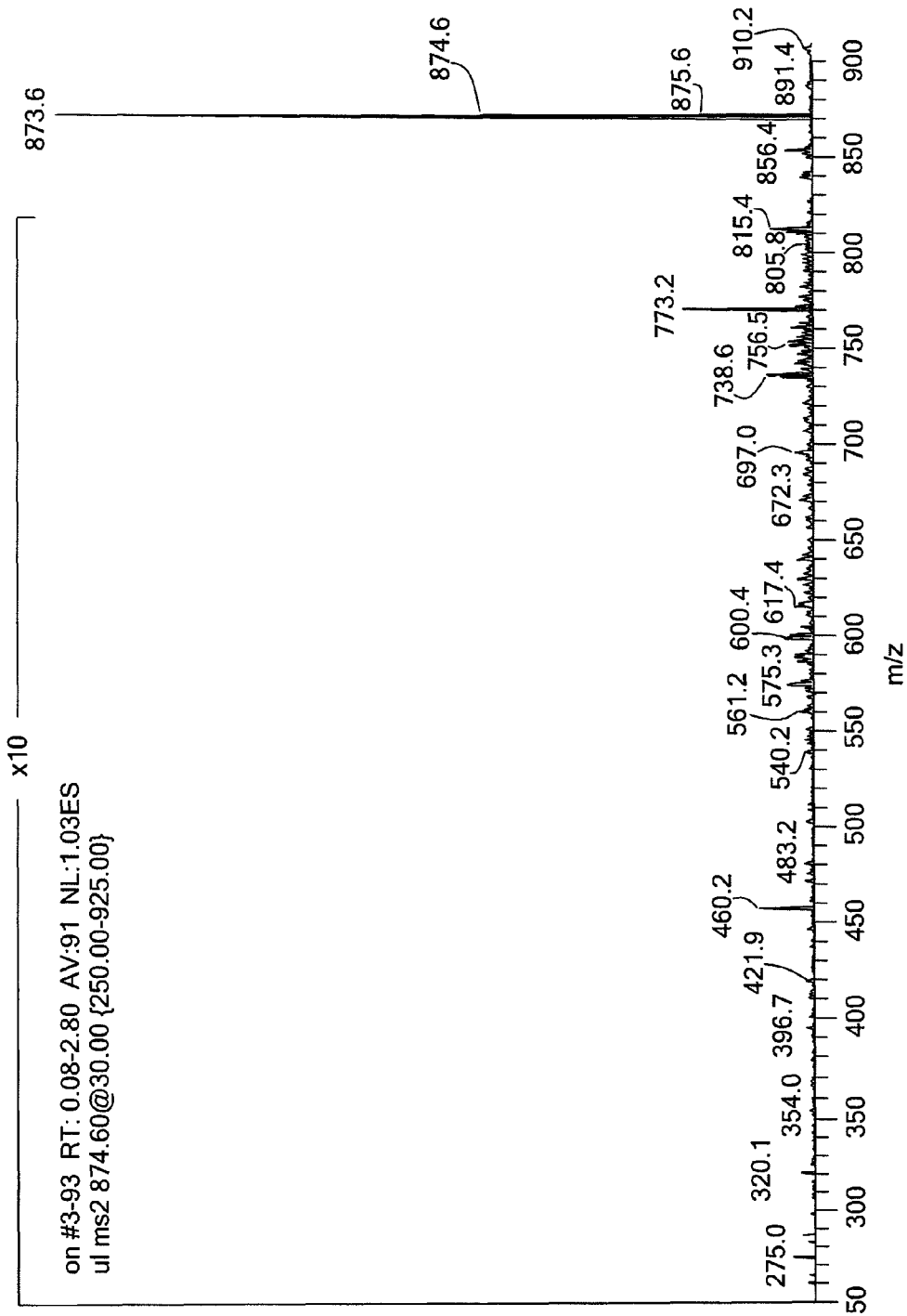
FIG. 6 is a trace showing detection by mass spectrometry of 25 fmol of deoxyadenosine-5'-monophosphate labeled with molecular tag 6 according to the invention.

Detection of deoxyadenosine-5'-monophosphate (5' dAMP) Using the Method of the Invention Very sensitive detection of 25 fmol at S/N=50 of an INLT-labeled analyte compound by tandem mass spectrometry (ThermoFinnigan LCQ) is shown in FIG. 6, in which a predominant loss of neutral Et$_3$N from the parent ion leads to an intense, analyte-characteristic daughter ion at m/z 773.

Two mg of INLT tag 6, 3 mg 5' dAMP, 20 mg EDAC, and 1 ml of 0.2 M MES buffer, pH 6.2 were mixed in a plastic vial. The reaction mixture was kept at room temperature for 4 hr, and 20 µl was injected into HPLC. The product peak (compound 7, the phosphorimidazolide conjugate of INLT 6 and 5'-dAMP) was collected, and the concentration of the collected solution was determined with UV spectrometry at 260 nm, assuming the molar extinction coefficient of product was the same as that of dAMP (1.34e4). A solution of $1 \times 10^{-8}$ M of 7 in methanol:H$_2$O, 1:1, was infused into an LCQ electrospray mass spectrometer (Thermo Finnigan) over a 2.5 minute period (25 fmol of 7). MS/MS spectra were accumulated over this period relying on continued isolation and collisionally-induced dissociation of M$^+$ (874.5 u), forming, through loss of (CH$_3$CH$_2$)$_3$N, daughter ion 773.3 u. The mass spectrum is shown in FIG. 6. S/N (signal to noise ratio) for the latter ion is >50. Source conditions for electrospray: capillary temperature: 250° C.; sheath gas: 20 units; auxiliary gas: 0 units; spray voltage: 4.5; collision energy: 23 units.

EXAMPLE 4

Ultrasensitive Detection of an INLT-Labeled Analyte Compound

Figure 7:
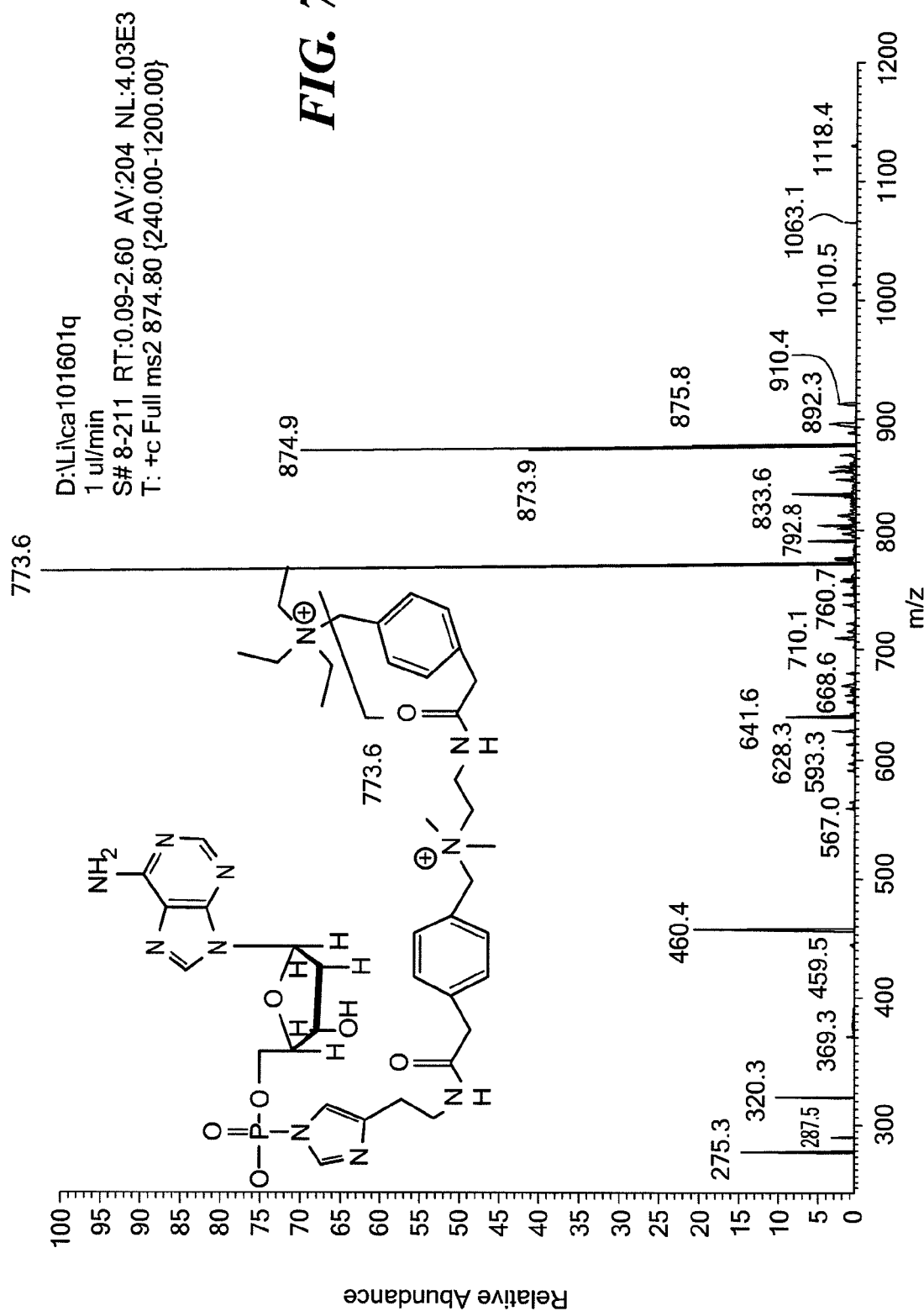
FIG. 7 is a trace showing detection by mass spectrometry of 500 amol of deoxyadenosine-5'-monophosphate labeled with molecular tag 6 according to the invention.

FIG. 7 further demonstrates the ultrasensitivity of detection of an INLT-labeled analyte compound according to the invention an INLT tag. To obtain this mass spectrum, 0.5 µl of $1 \times 10^{-9}$ M (500 amol) of compound 7 was infused into a tandem electrospray ion trap mass spectrometer (Thermo Finnigan Deca XP), a related, more modern instrument compared to the mass spectrometer used in Example 3. Compound 7 was detected at m/z 773, analogous to its detection in Example 3.

REFERENCES

Dear G. J., J. Ayrton, R. Plumb, I. J. Fraser (1999) The *Rapid Identification of Drug Metabolites Using Capillary Liquid Chromatography Coupled to an Ion Trap Mass Spectrometer*, Rapid Commun. Mass Spectrom., 13, 456-463.

Goldacre, R. J., Phillips, J. N., *J. Chem. Soc.* (1949) 1724; Deno, N. C., Schriesheim, *A. J. Am. Chem. Soc.* (1955) 77, 3051.

Goldacre, R. J., Phillips, J. N., *J. Chem. Soc.* (1949) 1724; Deno, N. C., Schriesheim, *A. J. Am. Chem. Soc.* (1955) 77, 3051.

Johnson D. W., *Alkyldimethylaminoethyl ester iodides for improved analysis of fatty acids by electrospray ionization tandem mass spectrometry*, Rapid Commun. Mass Spectrom, 14, 2019-2924, 2000.

Rappsilber J., H. Steen, M. Mann, *Labile sulfogroup allows differentiation of sulfotyrosine and phosphotyrosine in peptides*, J. Mass Spectrom. 2001, 36, 832-833.

Roth K. D. W., Z.-H. Huang, N. Sadagopan, J. T. Watson (1998) *Charge Derivatization of Peptides for Analysis by Mass Spectrometry, Mass Spectrom.* Rev. 17, 255-274.

Thompson et al., *Tandem Mass Tags: A Novel Quantification Strategy for Comparative Analysis of Complex Protein Mixtures by MS/MS*, Anal. Chem. 2003, 75, 1895-1904.

Zaia J. and K. Biemann, *Comparison of Charged Derivatives for High Energy Collision-Induced Dissociation tandem Mass Spectrometry*, J. Am. Soc. Mass. Spectrom. 1995, 6, 428-436.

Zhang H. and J. Henion *Quantitative and Qualitative Determination of Estrogen Sulfates in Human Urine by Liquid Chromatography/Tandem Mass Spectrometry Using 96-Well Technology*, Anal. Chem. 1999, 71, 3955-3964.

Zhao Y., S. B. H. Kent, B. T. Chait (1997) *Rapid, sensitive structure analysis of oligosaccharides*, Proc. Natl. Acad. Sci. 94, 1629-1633.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. The molecular tag 4-(sulfonyloxy)benzoic acid NHS ester.

2. A molecular tag for detection of an analyte (A) by tandem mass spectrometry, said molecular tag being of the form:
XxyYZ, wherein
Z is a reactivity group that, as part of a tandem mass spectrometry analysis procedure, is capable of attaching covalently to analyte (A) to form product XxyYZ-A;
Xxy is a sulfate or carbonate containing one or more $^{18}O$ atoms;
Y is a group comprising an unsaturated group;
x and y are atoms that are connected to each other by a single bond; and, in the group yY,
y is connected to an unsaturated group of Y by a single bond.

3. The molecular tag of claim 2, wherein Y comprises a phenyl group.

4. The molecular tag of claim 2, wherein Y comprises a phenyl group conjugated to a carbonyl group.

5. The molecular tag of claim 2, wherein yY comprises one or more $^2H$, $^{15}N$, $^{13}C$ or $^{18}O$ atoms.

6. A molecular tag for detection of an analyte (A) by tandem mass spectrometry, said molecular tag being of the form:
XxyYZ, wherein
Z is a reactivity group that, as part of a tandem mass spectrometry analysis procedure, is capable of attaching covalently to analyte (A) to form product XxyYZ-A;
Xxy is a carbonate group;
Y is a group comprising an unsaturated group;
x and y are atoms that are connected to each other by a single bond; and, in group yY,
y is connected to an unsaturated group of Y by a single bond.

7. The molecular tag of claim 6, wherein Y comprises a phenyl group conjugated to a carbonyl group.

8. The molecular tag of claim 6, wherein Xxy contains one or more $^{13}C$ or $^{18}O$ atoms.

9. The molecular tag of claim 6, wherein yY contains one or more $^2H$, $^{15}N$, $^{13}C$ or $^{18}O$ atoms.

10. A molecular tag for detection of an analyte (A) by tandem mass spectrometry, said molecular tag being of the form:
XxyYZ, wherein
Z is a reactivity group that, as part of a tandem mass spectrometry analysis procedure, is capable of attaching covalently to analyte (A) to form product XxyYZ-A;
Xxy is a sulfate;
Y is a group comprising an unsaturated group;
x and y are atoms that are connected to each other by a single bond; and, in the group, yY,
y is connected to an unsaturated group of Y by a single bond, wherein Y comprises a phenyl group conjugated to a carbonyl group.

11. The molecular tag of claim 10, wherein Xxy contains one or more $^{18}O$ atoms.

12. The molecular tag of claim 10 wherein yY contains one or more $^2H$, $^{13}C$, $^{15}N$ or $^{18}O$ atoms.

13. A molecular tag for detection of an analyte (A) by tandem mass spectrometry, said molecular tag being of the form:
XxyYZ, wherein
Z is a reactivity group that, as part of a tandem mass spectrometry analysis procedure, is capable of attaching covalently to analyte (A) to form product XxyYZ-A;
Xxy comprises a quaternary amine containing one or more 0 atoms, or two or more N atoms, wherein x is a nitrogen atom that bears a positive charge;
Y is a group comprising an unsaturated group;
x and y are atoms that are connected to each other by a single bond; and, in the group yY,
y is connected to an unsaturated group of Y by a single bond.

14. The molecular tag of claim 13, wherein Xxy or yY contains one or more $^2H$, $^{13}C$, $^{15}N$ or $^{18}O$ atoms.

15. A molecular tag for detection of an analyte (A) by tandem mass spectrometry, said molecular tag being of the form:
XxyYZ, wherein Z is a reactivity group that, as part of a tandem mass spectrometry analysis procedure, is capable of attaching covalently to analyte (A) to form product XxyYZ-A;

Xxy comprises two or more quaternary amines, wherein x is a nitrogen atom that bears a positive charge;

Y is a group comprising an unsaturated group;

x and y are atoms that are connected to each other by a single bond; and, in the group yY, y is connected to an unsaturated group of Y by a single bond.

16. The molecular tag of claim 15, wherein Y comprises a phenyl group.

17. The molecular tag of claim 15, wherein yY comprises an allyl or propargyl group.

* * * * *

UNITED STATES PATENT AND TRADEMARK OFFICE
CERTIFICATE OF CORRECTION

| | | |
|---|---|---|
| PATENT NO. | : 7,947,511 B2 | Page 1 of 1 |
| APPLICATION NO. | : 12/479283 | |
| DATED | : May 24, 2011 | |
| INVENTOR(S) | : Poguang Wang et al. | |

It is certified that error appears in the above-identified patent and that said Letters Patent is hereby corrected as shown below:

Column 8, line 59, "in ml" should read -- in 5ml --;

Column 10, line 43, "M" should read -- "M" --; and

Column 12, claim 13, line 54, "0 atoms," should read -- O atoms, --.

Signed and Sealed this

Thirteenth Day of December, 2011

David J. Kappos
*Director of the United States Patent and Trademark Office*